(12) United States Patent
Paul et al.

(10) Patent No.: US 8,900,193 B2
(45) Date of Patent: Dec. 2, 2014

(54) FAST-ACTING OR ROTATING TRANSSEPTAL NEEDLE

(75) Inventors: Saurav Paul, Minneapolis, MN (US); Todd R. Stangenes, Minneapolis, MN (US); Reed R. Heimbecher, Hamel, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 428 days.

(21) Appl. No.: 13/142,957

(22) PCT Filed: Dec. 23, 2009

(86) PCT No.: PCT/US2009/069433
§ 371 (c)(1),
(2), (4) Date: Jun. 30, 2011

(87) PCT Pub. No.: WO2010/078196
PCT Pub. Date: Jul. 8, 2010

(65) Prior Publication Data
US 2011/0270191 A1 Nov. 3, 2011

Related U.S. Application Data

(60) Provisional application No. 61/141,789, filed on Dec. 31, 2008.

(51) Int. Cl.
*A61M 5/178* (2006.01)
*A61B 17/34* (2006.01)
*A61B 17/00* (2006.01)

(52) U.S. Cl.
CPC ... *A61B 17/3478* (2013.01); *A61B 2017/00243* (2013.01)
USPC .................. 604/164.12; 604/167.03; 606/185

(58) Field of Classification Search
CPC ........... A61B 17/3421; A61B 17/3478; A61B 17/3494; A61B 2017/00243; A61M 25/06; A61M 25/0631; A61M 25/0666; A61M 25/0662; A61M 25/065
USPC ........................ 604/164.01–170.03; 606/185
See application file for complete search history.

(56) References Cited

U.S. PATENT DOCUMENTS

| 5,163,916 | A | 11/1992 | Sunderland |
| 5,318,583 | A | 6/1994 | Rabenau et al. |
| 5,384,945 | A | 1/1995 | Spingler |
| 6,077,248 | A * | 6/2000 | Zumschlinge ........... 604/167.01 |
| 6,488,693 | B2 * | 12/2002 | Gannoe et al. ................ 606/167 |
| 6,752,814 | B2 * | 6/2004 | Gellman et al. .............. 606/148 |
| 7,419,496 | B2 * | 9/2008 | Staudner ....................... 606/185 |
| 7,632,262 | B2 * | 12/2009 | Bates ............................ 604/508 |
| 2008/0214889 | A1 | 9/2008 | Saadat et al. |

* cited by examiner

OTHER PUBLICATIONS

"PCT Search Report & Written opinion", PCT/US2009/069433 Mar. 11, 2010.

*Primary Examiner* — Matthew F Desanto
(74) *Attorney, Agent, or Firm* — Dykema Gossett PLLC

(57) ABSTRACT

A transseptal medical device (10, 110) is provided including a dilator (12, 112), a needle (14, 114), and a needle control mechanism (22, 122). The needle (14, 114) may be disposed within the dilator (12, 112), and the needle control mechanism (22, 122) may be operably connected to a proximal end (24, 124, 16, 116) of the needle (14, 114) or the dilator (12, 112) for selective adjustment of the distal end (26, 126) of the needle (14, 114) from a first position within the dilator (12, 112) to a second position external to the dilator (12, 112). The needle control mechanism (22) may include an actuator (32) configured for rotation within the dilator in one embodiment.

13 Claims, 3 Drawing Sheets

FAST-ACTING OR ROTATING TRANSSEPTAL NEEDLE

CROSS-REFERENCE TO RELATED APPLICATIONS

This application claims the benefit of U.S. provisional application No. 61/141,789, filed 31 Dec. 2008 (the '789 application), which is hereby incorporated by reference. This application is a national stage filing based upon international application no. PCT/US2009/069433, filed 23 Dec. 2009 and published in English on 8 Jul. 2010 under international publication no. WO 2010/078196 A1 (the '433 application), which claims priority to the '789 application.

BACKGROUND OF THE INVENTION a. Field of the Invention

The instant invention relates to assemblies and methods for puncturing, or piercing, tissue within the body, including, for example, transseptal access systems and methods for accessing the left atrium.

b. Background Art

The human heart includes a right ventricle, a right atrium, a left ventricle and a left atrium. The right atrium is in fluid communication with the superior vena cava and the inferior vena cava. The tricuspid valve separates the right atrium from the right ventricle. The right atrium is separated from the left atrium by the intra-atrial septum. The intra-atrial septum includes a thin membrane known as the fossa ovalis. The human heart further includes the left superior pulmonary vein, the left pulmonary artery, the arch of the aorta, and the right pulmonary artery.

A wide variety of diagnostic and therapeutic procedures have been developed in which a catheter is transluminally advanced within a guide sheath or over a guidewire into various chambers and across valves of the heart. The most difficult chamber of the heart to access with a catheter may be the left atrium. Access to the left atrium through the pulmonary artery may not be possible. Approaches from the left ventricle are difficult, may cause arrhythmias and may present difficulty in obtaining stable catheter positioning. Accordingly, one of the most common approaches used by electrophysiologists to gain access to the left atrium is through puncture of the intra-atrial septum. This procedure is commonly referred to as transseptal catheterization. The manual puncture of the intra-atrial septum is generally performed at the location of the fossa ovalis.

The objectives of left atrial access can be either diagnostic or therapeutic. One therapeutic use is electrophysiological intervention, e.g., left atrial ablation. Catheter ablation involves the placement of energy (typically RF) through a catheter, into various locations of the heart to eradicate inappropriate electrical pathways affecting the heart function. When these locations are in the left atrium, the catheter through which the RF generator is placed typically is itself placed through trans septal catheterization.

In most cases, transseptal catheterization is facilitated with tools such as a sheath, dilator, and a needle. The conventional approach for trans septal catheterization follows a number of steps. First, a guidewire is introduced into the femoral vein (or other pathway of choice) and is manipulated into the inferior vena cava (IVC). Second, a sheath typically having a dilator disposed therein are inserted over the proximal end of the guidewire and are fed into the IVC. At this point, the guidewire is removed. Third, a needle is advanced through the inner lumen of the dilator with the distal end still inside of the distal end of the dilator. In what is typically referred to as a trans septal approach, a needle may be pressured though the intra-atrial septum between the right and left atria by a physician using the needle. With the needle still contained within the distal end of the dilator, the needle is maneuvered into the right atrium and pulled along the septal wall of the right atrium until it is proximate the fossa ovalis. The needle is then advanced forward by the physician through the dilator to puncture the septal wall. Upon confirmation of the puncture, the dilator and sheath can then be fed through the septal wall over the needle, thereby accessing the left atrium. The needle opening may be expanded so that various tools (e.g., sheaths or catheters) may be pressed through the opening and have access to the left atrium and the pulmonary veins. After the tools are positioned in the left atrium, various procedures, such as ablation and mapping, may be performed therein.

As described above, conventional methods of gaining access to the left atrium involve manually puncturing the intra-atrial septum at the location of the fossa ovalis using a needle. Although this method is frequently used and clinically accepted, there are some potential risks to the patient. In particular, complications may be encountered if the septal tissue is exceptionally thick or exhibits increased compliance.

The septal wall, and particularly the fossa ovalis, is a compliant structure. Generally, the fossa ovalis is even more compliant than the septal wall. Consequently, when a needle contacts the septal tissue, the contact force causes the tissue to stretch and displace in the direction of the applied force. The displacement of the tissue may be proportional to the applied force and the compliance of the tissue (e.g., displacement per unit force). Accordingly, the greater the applied force, the greater the displacement. When the contact force applied by the needle against the tissue is gradually increased (thereby increasing the contact pressure, which is force divided by area), the tissue displaces more and more in response to the force until the force is high enough to create a contact pressure that exceeds the breaking stress of the tissue wall, thereby causing a hole in the wall allowing the needle to pierce through the wall. In order to improve the safety and efficacy of transseptal puncture, it may be desirable to increase the contact pressure (e.g., beyond the breaking stress of the fossa ovalis), while minimizing the displacement of the compliant fossa ovalis.

In the case of a thick and/or fibrous septum, a physician may need to apply a large force to the needle to advance the needle through the septum. When the needle exits the septal tissue, it may be difficult to stop its forward movement because of the large force that has been applied. This may result in inadvertent puncture of the left atrial free wall. Similarly, in the case of exceptionally compliant septal tissue, the needle may be advanced too far into the left atrium while tenting the fossa ovalis prior to puncture. The proximity of the needle tip to the left atrial free wall may increase the risk of perforation when force is applied to gain access. As the needle exits the septal tissue it may already be in contact with additional structures within the left atrium.

It may be desirable to provide features to avoid unnecessary punctures or mistakes during operation of the transseptal needle.

BRIEF SUMMARY OF THE INVENTION

It is desirable to be able to ensure effective puncture of septal tissue of increased thickness or compliance without resorting to the application of a large axial force leading to significant displacement of the fossa ovalis.

The invention includes a transseptal medical device comprising: a dilator having a proximal end and a distal end and a needle disposed within the dilator, the needle having a proximal end and a distal end. The transseptal medical device further comprises a needle control mechanism operably connected to the proximal end of the needle or the dilator for selective adjustment of the distal end of the needle from a first position within the dilator to a second position external to the dilator.

The invention further includes a method of puncturing a septum of a heart. The method may include the steps of introducing a needle disposed within a dilator into an area of the heart proximate a target area of the septum; extending a portion of the needle to a position external to the dilator proximate the target area of the septum through partial rotation of an actuator and compression of a spring disposed within the dilator; puncturing the target area of the septum; and retracting the needle to a position within the dilator through completing rotation of the actuator and unbiasing (decompressing) the compression spring disposed within the dilator. In one example, the needle may be rotated while puncturing the target area of the septum.

The foregoing and other aspects, features, details, utilities, and advantages of the present invention will be apparent from reading the following description and claims, and from reviewing the accompanying drawings.

DETAILED DESCRIPTION OF THE INVENTION

Generally, the instant invention relates to improved assemblies and methods used in transseptal catheterization procedures. The assemblies and methods may be used for accessing the left atrium from the right atrium by crossing the intra-atrial septum. Accordingly, the inventive assemblies and methods may be configured to improve left-heart access tools, including transseptal needle assemblies, to ensure an effective puncture of the septal tissue.

Figure 1:
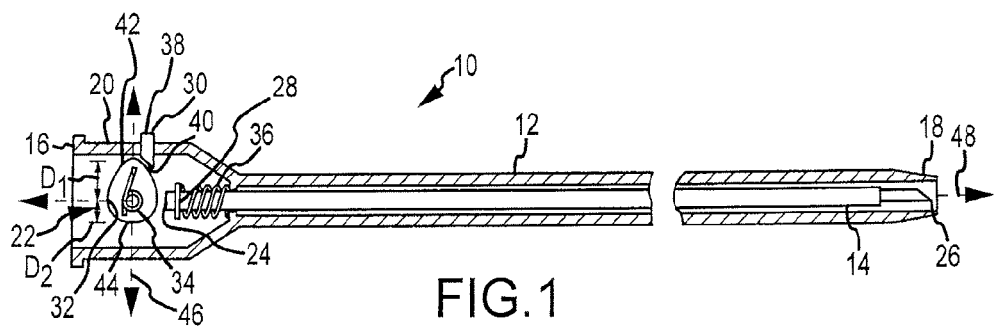
FIG. 1 is a partial sectional view of a needle and dilator assembly in accordance with a first embodiment of the invention, in which the needle tip is in an inwardly-biased (i.e., un-deployed) position and is retracted within the distal end of the dilator.
Figure 2:
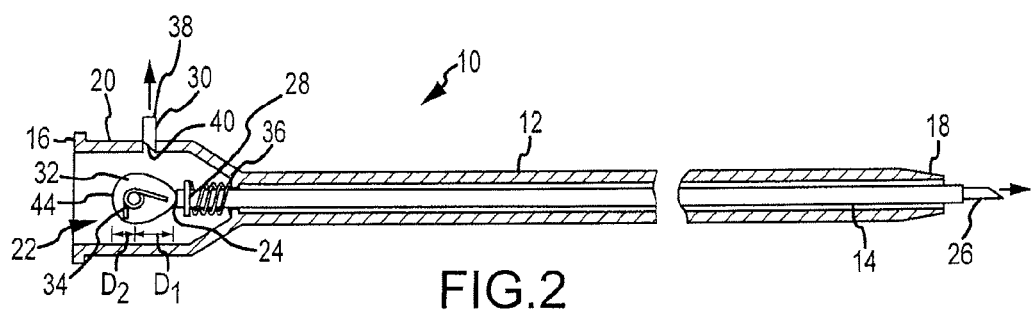
FIG. 2 is a partial sectional view of the needle and dilator assembly of FIG. 1 in which the needle tip is in an outwardly-biased (i.e., deployed) position and is extended beyond the distal end of the dilator.
Figure 3:
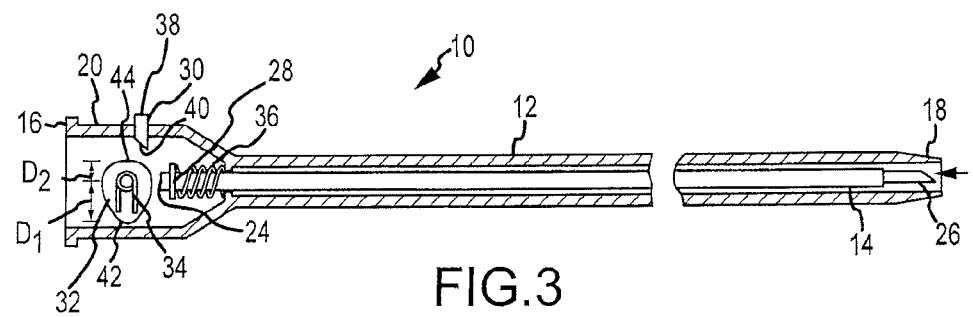
FIG. 3 is a partial sectional view of the needle and dilator assembly of FIGS. 1-2 in which the needle is moved back to its inwardly-biased position and is retracted within the distal end of the dilator.

Conventional transseptal procedures utilize several, separate components including a sheath, a dilator, and a needle. Referring now to FIGS. 1-3, an assembly 10 in accordance with one embodiment of the present invention may include a dilator 12 and a needle 14. The assembly 10 may comprise a medical device and may be configured to have at least a portion that is disposed within a sheath (not shown). Both the dilator 12 and the needle 14 may be disposed within the inner lumen of the sheath in an embodiment. The sheath may comprise an elongate tubular member having a proximal end and a distal end. The sheath may include a sheath hub at the proximal end. The sheath may be preconfigured with a bend at an angle desirable for use with transseptal catheterization procedures.

The dilator 12 may comprise an elongate tubular member having a proximal end 16 and a distal end 18. The dilator 12 may include a dilator hub 20 at the proximal end 16. For example, and without limitation, the dilator 12 may comprise a flexible material, such as biocompatible polymers, plastics, braided wire assemblies, and/or combinations thereof, or any other suitable material known to those of ordinary skill in the art. For example and without limitation, dilator 12 may comprise biocompatible polymeric materials, such as high density polyethylene, polytetrafluorethylene (PTFE), nylons, or any other materials known in the art, and/or a combination thereof. The dilator 12 may comprise a spring coil, stainless steel, NiTi alloys, or a braided reinforced wall, and/or any combination thereof in other embodiments. The dilator 12 may have an approximately circular cross-section in some embodiments. The dilator 12 may have a substantially similar diameter throughout the length of its shaft in some embodiments. The distal end 18 of the dilator 12 may have a cross-sectional dimension that is smaller than a cross-sectional dimension of the proximal end 16 of the dilator 12 in some embodiments. The distal end of the dilator 12 may be tapered in some embodiments, but the cross-sectional dimension of the inner lumen may remain the same through the length of the shaft. The dilator 12 may be approximately 60 cm to approximately 120 cm in length in some embodiments. However, the dilator 12 may be shorter or longer in other embodiments. The overall length of the dilator 12 may depend upon the percutaneous access point and the desired applications. For example, lengths in the area of from about 80 cm to about 100 cm may be typical for use in percutaneous transluminal access at the femoral vein for locating and puncturing a site on the atrial septum in the heart. Other lengths and diameters may be utilized depending upon the desired performance of the dilator 12. The distal end 18 of the dilator may be similar to conventional dilators used in transseptal catheterization procedures. However, the hub 20 at the proximal end 16 of the dilator 12 may be modified to fit a needle control mechanism 22 as described herein.

The needle 14 may be of construction that is similar to conventional needles used in trans septal catheterization procedures. The needle may have a proximal end 24 and a distal end 26. The needle 14 may include a needle hub 28 at the proximal end 24. For example, and without limitation, at least a portion of the shaft of the needle 14 may comprise stainless steel, a polymer, a plastic, a braid-reinforced polymer, or a coil in other embodiments. At least a portion of the needle 14 may be flexible in some embodiments. At least a portion of the needle 14 may be rigid in some embodiments. For example, the needle 14 may be rigid at the distal end 26 and/or at the proximal end 24. The needle 14 may be curved in some embodiments. The needle 14 may be approximately 60 cm to approximately 120 cm in length in some embodiments. However, the needle 14 may be shorter or longer in other embodiments. The needle 14 may have a length substantially equal to the length of the dilator 12 in some embodiments, or may be shorter or longer (e.g., even substantially shorter or longer) than the dilator 12 in other embodiments. The needle 14 may be disposed within the dilator 12 (e.g., within an inner lumen of the dilator 14). The needle may be moveable within the dilator 12. In one embodiment, the position of the needle 14 may be precisely locatable within the dilator 12. The needle 14 may be adjustable from a predetermined position within the shaft of the dilator 12 to a position extending beyond the distal end 18 of the dilator 12 when necessary for use of the needle 14 in transseptal procedures. Regardless of the length of the needle 14, the needle 14 may be capable of being extended by the needle control mechanism 22 to a position external of the distal end 18 of the dilator 12.

In some embodiments, the dilator hub 20 and the needle hub 28 may comprise a hand assembly that may be used by an operator. A sheath hub (not shown) may also make up the hand assembly that may be used by an operator. The dilator hub 20 and the needle hub 28 may be cooperatively configured and removably connected through any number of mechanical devices (e.g., a latch, a biased latch, a snap assembly, or any similar removable connection known in the art).

The assembly 10 may further include a needle control mechanism 22. The needle control mechanism 22 may be operably connected to the dilator 12 or the needle 14. The needle control mechanism 22 may allow for selective advancement of the needle 14 to various positions, including a retracted position within the distal end 18 of the dilator 12, as well as an extended position external to the distal end 18 of the dilator 12 for puncture purposes. In operation, the needle control mechanism 22 may be operably connected to the dilator 12 or the needle 14 such that when the needle control mechanism 22 is in a first position, the distal end 26 of the needle 14 is maintained at a predetermined, retracted position within the dilator 12. Referring now to FIG. 1, an assembly 10 including the dilator 12 and the needle 14, is illustrated. The distal end 26 (e.g., tip) of the needle 12 may be in an un-deployed position. In an un-deployed position, the distal end 26 of the needle 12 may be retracted and/or contained within the dilator 12 and may not extend beyond the distal end 18 of the dilator 12. Upon exertion of a force upon the needle control mechanism 22, the needle 14 may be extended from an initial position within the dilator 12 to a second position (e.g., a position external to the distal end 18 of the dilator 12). The extended position may be the desired position for puncture of tissue in the body (e.g., the intra-atrial septum).

The needle control mechanism 22 may be disposed at the proximal end 16 of the dilator 12 (i.e., at or within the dilator hub 20). The needle control mechanism 22 may be placed in whole or in part, near or proximate the dilator hub 20, the needle hub 28, and/or a sheath hub. The needle control mechanism 22 may comprise a latch 30 or any other mechanism known to those of skill in the art. The latch 30 may be accessible on a side of the dilator hub 20 or needle hub 28. As illustrated in FIG. 1, the latch 30 may be accessible on the side of the dilator hub 20. The latch 30 may comprise a button (e.g., a push-button) for engagement of the latch 30 by the user when the assembly 10 is in operation. While a button (e.g., push button) is mentioned in detail for advancing the needle, any other similar mechanism may be used, including, for example, a roller or sliding mechanism.

In one embodiment, the needle control mechanism 22 may comprise a latch 30, an actuator 32, a torsion spring 34, and a compression spring 36. Although this needle control mechanism 22 has been described in detail, the needle control mechanism 22 may comprise any alternative system that, upon action from an operator of the assembly 10, may work to move the needle 14 in an axial direction forward and backward. The latch 30 may be configured so that when it is moved, the actuator 32 is released and advances the needle 14 beyond the distal end of the dilator 12 (i.e., a needle deployed position) as shown in FIG. 2. The latch 30 may comprise a button (e.g., a push-button) for engagement and/or actuation of the latch 30 by the user when the assembly 10 is in operation. The latch 30 may include a first end 38 exposed for actuation by a user of the assembly 10. The latch 30 may include a second end 40 configured for engagement with actuator 32. The needle 14 may return to its first and/or original position within the distal end 18 of the dilator 12 (i.e., an un-deployed position), as shown in FIG. 3. The action of the distal end 26 of the needle 12 may leverage the principle of linear momentum and allow the needle 14 to more easily puncture the intra-atrial septum, including a thick and/or compliant intra-atrial septum. In particular, the fast rate of change of linear momentum may ensure that the needle 14 may puncture the septal wall (including fossa ovalis) without the application of excessive axial force leading to significant (and potentially dangerous) displacement of the fossa ovalis.

The actuator 32 may comprise a member with an oblong shape (i.e., any shape with a first distance $D_1$ between the torsion spring 34 and a first edge 42 of the actuator 32 that is different than a second distance $D_2$ between the torsion spring 34 and a second edge 44 of the actuator 32). For example and without limitation, the first distance $D_1$ may be greater than the second distance $D_2$. The latch 30 may be configured to control the actuator 32. For example, the latch 30 may hold the actuator 32 in place and prevent it from rotating, as shown in FIG. 1. Still referring to FIG. 1, the actuator 32 may be disposed in a first orientation (e.g., wherein a longitudinal axis 46 of actuator 32 is perpendicular to a longitudinal axis 48 of the assembly 10). The latch 30 may engage the actuator 32 proximate a first edge 42 of the actuator 32 and prevent the actuator 32 from rotating.

Torsion spring 34 may be configured to rotate actuator 32. Torsion spring 34 may be biased (i.e., held in a twisted configuration) when the actuator 32 is prevented from rotating, as shown in FIG. 1. When the latch 30 of the needle control mechanism 22 is pushed and/or otherwise engaged, the torsion spring 34 may be allowed to rotate the actuator 32. As shown in FIG. 2, the actuator 32 may be disposed in a second orientation (e.g., wherein a longitudinal axis 46 of actuator 32 is parallel to a longitudinal axis 48 of the assembly 10) after the actuator 32 begins to rotate. When the actuator 32 rotates, the needle 14 may be pushed forward (i.e., beyond the distal end 18 of the (i.e., held in a twisted configuration) dilator 12). Still referring to FIG. 2, the actuator 32 is shown after the actuator 32 has traveled about one half of its intended rotation (e.g., about 90° in one embodiment). Although about 90° is mentioned in detail as about one half of the intended and/or predetermined rotation of actuator 32, one half of the intended and/or predetermined rotation of actuator 32 may be increased or decreased in other embodiments.

Referring now to FIG. 3, the actuator 32 is shown after the actuator 32 has completed its intended rotation (e.g., about 1800 in one embodiment). Although about 1800 is mentioned in detail as the intended and/or predetermined rotation of actuator 32, the intended and/or predetermined rotation of actuator 32 may be increased or decreased in other embodiments. As shown in FIG. 3, the actuator may be disposed in a third orientation (i.e., wherein a longitudinal axis 46 of actuator 32 is again perpendicular to a longitudinal axis 48 of the assembly 10) after the actuator 32 has completed its intended rotation. However, the latch 30 may no longer engage actuator 32 since the latch 30 is now proximate a second edge 44 of the actuator 32. Still referring to FIG. 3, the needle 14 may be pushed backwards (inwardly in FIG. 3) by the compression spring 36 which may be back in an unbiased (decompressed) position. The torsion spring 34 may now be in an unbiased (untwisted) position as well. The fast rate of change of linear momentum may ensure that the needle 14 can puncture the septal wall effectively without the need to gradually apply large and/or excessive axial force, which may lead to significant and/or potentially dangerous displacement of the fossa ovalis.

Compression spring 36 may be configured to inwardly bias the needle 14. Compression spring 36 or another spring biased member may function as a safety mechanism. Although a compression spring 36 is mentioned in detail, other mechanisms may function as a safety mechanism, such as a clip spacer or another locking mechanism. Compression spring 36 may be operably connected to the needle 14. Compression spring 36 may be located at the proximal end 24 of the needle 14. In one embodiment, compression spring 36 may be located within an operable handle (e.g., within dilator hub 20 and/or needle hub 28). In other embodiments, compression spring 36 may be external to the dilator hub 20 and/or needle hub 28.

Compression spring 36 may allow for extension of the needle 14 beyond the distal end 18 of the dilator 12 only upon the affirmative action of the operator of assembly 10. Accordingly, the compression spring 36 may hold the needle 14 within the dilator when the needle control mechanism 22 is in an unbiased or locked position. As shown in FIG. 1, the compression spring 36 may be in an unbiased (i.e., uncompressed) position, so that the needle 14 may be fully contained within the distal end 18 of the dilator 12. In the inwardly-biased (i.e., un-deployed) position, the needle 14 may remain at a predetermined position within the dilator 12. When there is no force acting on the needle control mechanism 22, the needle 14 is at an initial, predetermined position within the dilator 12. The retracted position of the needle 14 within the dilator 12 may provide safety benefits over a needle that remains exposed beyond the distal end 18 of the dilator at all times. Upon activation of the needle control mechanism 22, the actuator 32 may rotate as described herein, and the compression spring 36 may be forced into a biased (i.e., compressed) configuration, as shown in FIG. 2. The compressed configuration of the compression spring 36 may allow the distal end 26 of the needle 14 to advance a predetermined distance and/or portion beyond the distal end 18 of the dilator 12. The distal end 26 of the needle 14 may be used for puncturing the intra-atrial septum. Referring now to FIG. 3, as the actuator completes its intended rotation, the compression spring 36 may be put back into an unbiased (i.e., uncompressed) configuration, which may cause the needle 14 to be pushed backward by the compression spring 36. The needle 14 may then be fully contained within the distal end 18 of the dilator 12.

The assembly 10 may further include additional features, such as one-way, two-way, or three-way valves (not shown) and/or access ports (not shown) for introduction or removal of fluids, such as contrast or saline fluids, and/or for pressure monitoring and safety devices. The number of valves and/or access ports may vary depending upon the functional capabilities required of assembly 10.

A method for puncturing a septum of a heart is also provided. The method may include the steps of introducing a needle disposed within a dilator into an area of the heart proximate a target area of the septum; extending a portion of the needle to a position external to the dilator proximate the target area of the septum through partial rotation of an actuator and compression of a spring disposed within the dilator; puncturing the target area of the septum; and retracting the needle to a position within the dilator through completing rotation of the actuator and unbiasing the spring disposed within the dilator.

Figure 4:
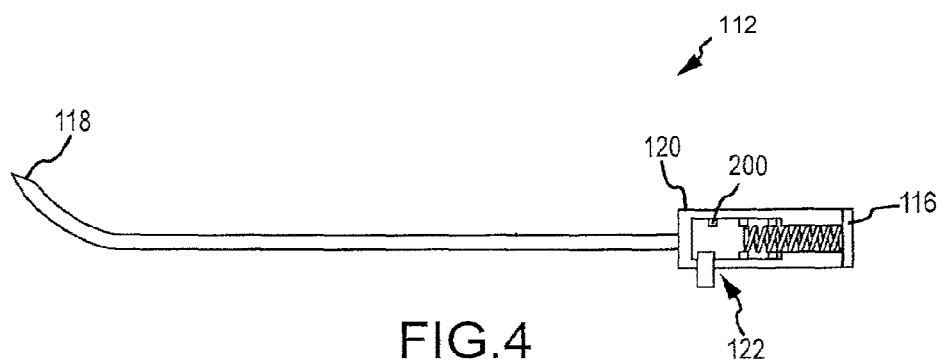
FIG. 4 is an isometric view of a dilator in accordance with a second embodiment of the invention with parts removed to reveal internal details.

In accordance with a second object of the invention, the assembly 110 may comprise a medical device including dilator 112 and a needle 114 as illustrated in FIGS. 4-7. Referring now to FIG. 4, an isometric view of the dilator 112 is illustrated. The dilator 112 may comprise an elongate tubular member having a proximal end 116 and a distal end 118. The dilator 112 may include a dilator hub 120 at the proximal end 116. Still referring to FIG. 4, the dilator 112 may be substantially similar to dilator 12, but its hub 120 at proximal end 116 may be modified to fit a needle control mechanism 122 as described herein and to include and/or incorporate internal threads 200. The internal threads 200 may comprise, for example and without limitation, corkscrew shaped threads or a helical structure. The size, shape, and orientation of the internal threads can be varied and/or adjusted depending upon the desired amount of rotation to minimize resistance during puncture and ensure effective puncture.

Figure 5:
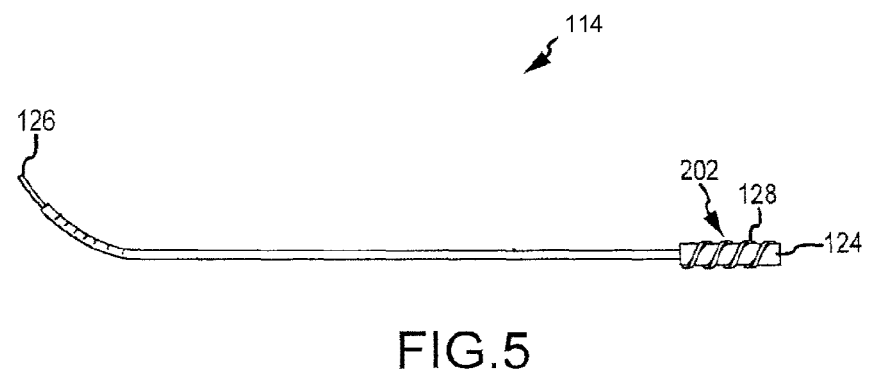
FIG. 5 is an isometric view of a needle in accordance with the second embodiment of the invention with parts removed to reveal internal details.

Referring now to FIG. 5, a perspective view of the needle 114 is illustrated. The needle 114 may have a proximal end 124 and a distal end 126 and may further include a needle hub 128 at the proximal end 124 of the needle 114. Still referring to FIG. 5, the needle 114 may be substantially similar to needle 14, but may be modified to include and/or incorporate external threads 202 and also the distal end 126 of the needle 114 may be laser cut to allow for the shaft of the needle 114 to rotate while in a curved shape (i.e., to translate rotation around the curve of the needle 114). The external threads 202 may comprise, for example and without limitation, corkscrew shaped threads or a helical structure. The size, shape, and orientation of the external threads 202 may be varied and/or adjusted depending upon the desired amount of rotation. The amount of rotation may be utilized to minimize resistance during puncture and ensure effective puncture without the need for the operator to apply large and/or excessive axial force. The internal threads 200 and the external threads 202 should correspond to each other in accordance with an embodiment of the invention. The correspondence of internal threads 200 and external threads 202 may ensure that the needle 114 may rotate within the dilator 112. The needle 114 may penetrate the fossa ovalis by rotating while moving transversely through the septal tissue.

Figure 6:
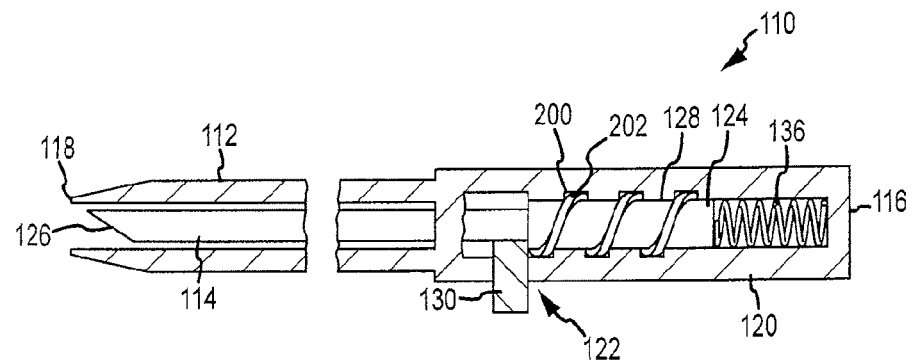
FIG. 6 is a partial sectional view of an assembly including the needle of FIG. 4 and the dilator of FIG. 5, and including the mechanism used to the control the needle in an inwardly-biased (i.e., needle un-deployed) position.
Figure 7:
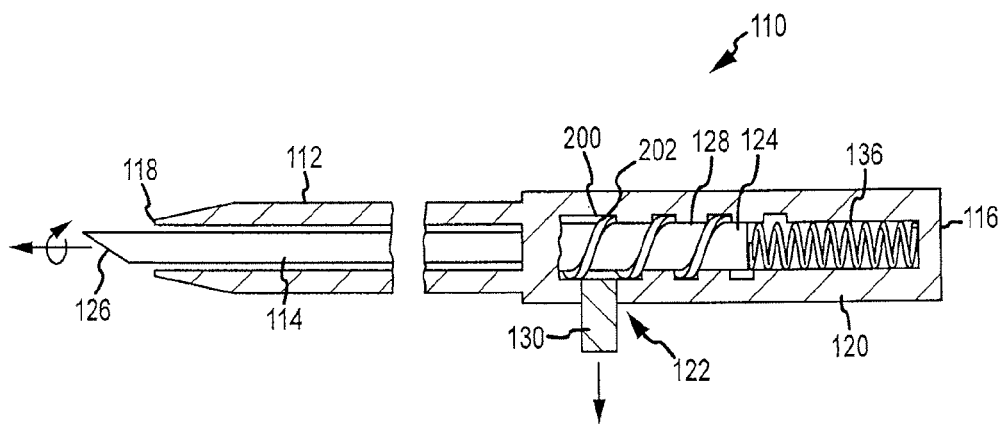
FIG. 7 is a partial sectional view of the assembly of FIG. 6, showing the mechanism used to the control the needle in an outwardly-biased (i.e., needle deployed) position.

Referring to FIGS. 6-7, the assembly 110 may further include a needle control mechanism 122. The needle control mechanism 122 may be operably connected to the dilator 112 or the needle 114. The needle control mechanism may allow for selective advancement of the needle 114 to various positions, including a retracted position within the distal end 118 of the dilator 112 as shown in FIG. 6, and an extended position external to the distal end 118 of the dilator 112 for puncture purposes as shown in FIG. 7. In operation, the needle control mechanism 122 may be operably connected to the dilator 112 or the needle 114 such that when the needle control mechanism 122 is in a biased (constrained) position, the distal end 126 of the needle 114 is maintained at a predetermined, retracted position within the dilator 112. The needle 114 is thus in an inwardly-biased (i.e., un-deployed) position and does not extend beyond the distal end 118 of the dilator 112. Upon actuation of the needle control mechanism 122, the needle 114 may be extended from a first or an initial position within the dilator 112 to a second position external to the distal end 118 of the dilator 112. The second or extended position may be the desired position for puncture of tissue in the body (e.g., the intra-atrial septum).

The needle control mechanism 122 may be disposed at the proximal end 116 of the dilator 112 and/or at the dilator hub 120. The needle control mechanism 122 may comprise a latch 130 or any other mechanism known to those of skill in the art and a compression spring 136 to locate the proximal end 124 of the needle 114. The latch 130 may be accessible on the side of the dilator hub 120 or needle hub 128. The latch 130 may comprise a button (e.g., a push-button) for engagement of the latch 130 by the user when the assembly 110 is in operation. While a button (e.g., push button) is mentioned in detail for advancing the needle, any other similar mechanism may be used, including, for example, a roller or sliding mechanism. The latch 130 may be configured for engagement with the needle 114 to hold the needle 114 in an inwardly-biased (e.g., un-deployed) position. Accordingly, the latch 130 may be configured to keep the needle 114 within the dilator 112 (i.e., in an inwardly-biased and/or un-deployed position) by keeping the compression spring 136 in a biased (i.e., compressed) position as shown in FIG. 6. The latch 130 may then be configured for actuation (e.g., a force or release) so that the latch 130 is no longer in engagement with the needle 114 as shown in FIG. 7. The needle 114 may then be put into an outwardly-biased (e.g., deployed) position when the needle 114 is extended beyond the distal end 118 of the dilator 112. When the latch 130 is actuated, the needle 114 may advance beyond the distal end 118 of the dilator 112. In accordance with this embodiment of the invention, the needle 114 may advance beyond the distal end 118 of the dilator 112 while rotating. This rotation may leverage the principle of angular momentum and allow the needle to more easily puncture the intra-atrial septum.

The needle control mechanism 122 may further include the compression spring 136. The compression spring 136 may be configured to bias the needle 114. Although a compression spring 136 is mentioned in detail, other mechanisms, such as a clip spacer or another locking mechanism may be used for biasing the needle 114. The compression spring 136 may be operably connected to the needle 114. The compression spring 136 may be located at the proximal end 124 of the needle 114. In one embodiment, the compression spring 136 may be located within dilator hub 120. However, in other embodiments, the compression spring 136 may be external to the dilator hub 120. The compression spring 136 may provide for extension of the needle 114 beyond the distal end 118 of the dilator 112 only upon the affirmative action of the operator of assembly 110. Accordingly, the latch 130 may hold the needle 114 within the dilator 112 when the compression spring 136 is in a biased (i.e., compressed) position. The retracted position of the needle 114 within the dilator 112 may provide significant safety benefits over a needle that remains exposed beyond the distal end 118 of the dilator 112 at all times. Upon actuation of the latch 130 of the needle control mechanism 122, the compression spring 136 may be forced into an unbiased (i.e., uncompressed) position, causing the needle 114 to be deployed (e.g., advance a predetermined distance and/or portion beyond the distal end 118 of the dilator 112). The distal end of the needle 114 may be used for puncturing the intra-atrial septum. The latch 130 may be configured to be actuated, thereby allowing the spring force of the compression spring 136 to push the needle 114 forward (e.g., beyond the distal end 118 of the dilator 112) as shown in FIG. 7. The needle 114 is thus in an outwardly-biased (e.g., deployed) position. As the needle 114 is moved forward, it may be forced to rotate due to the interaction of the external threads 202 on an exterior surface of the proximal end 124 of the needle 114 and the internal threads 200 on an inner surface of the proximal end 116 of the dilator 112. Travel of the needle hub 128 may dictate the distance that the distal end 126 of the needle 114 extends beyond the distal end 118 of the dilator 112. The rotation of the needle 114 may utilize angular momentum in order to ensure that the needle 114 will be able to puncture the septal tissue effectively without the need to apply large and/or excessive axial force.

The assembly 110 may further include additional features, such as one-way, two-way, or three-way valves (not shown) and/or access ports (not shown) for introduction or removal of fluids, such as contrast or saline fluids, and/or for pressure monitoring and safety devices. The number of valves and/or access ports may vary depending upon the functional capabilities required of assembly 110.

A method for puncturing a septum of a heart is also provided. The method may include the steps of introducing a needle disposed within a dilator into an area of the heart proximate a target area of the septum; extending a portion of the needle to a position external to the dilator proximate the target area of the septum; puncturing the target area of the septum; and retracting the needle to a position within the dilator. The method may further include the step of rotating the needle while puncturing the target area of the septum. Rotation of the needle may be accomplished through use of corresponding threads on the interior surface of the proximal end 116 of the dilator 112 and on the exterior surface of the proximal end 124 of the needle 114.

Although two embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A transseptal medical device, comprising:
a dilator having a proximal end and a distal end;
a needle disposed within the dilator, the needle having a proximal end and a distal end; and
a needle control mechanism operably connected to at least one of the proximal end of the needle and the dilator for selective adjustment of the distal end of the needle from a first position within the dilator to a second position external to the dilator, wherein the needle control mechanism comprises the following:
a latch, the latch including a portion external to the dilator;
an actuator configured for engagement with the latch, wherein the actuator is configured to undergo a predetermined amount of rotation while making intermittent contact with the needle; wherein the actuator is configured to engage the latch in a first actuator orientation and is configured to avoid engagement with the latch in a second actuator orientation following at least part of the predetermined amount of rotation of the actuator; and a torsion spring for rotating the actuator.

2. The transseptal medical device of claim 1, wherein the needle control mechanism further comprises a compression spring.

3. The transseptal medical device of claim 2, wherein the compression spring is unbiased when the actuator is in the first orientation.

4. The transseptal medical device of claim 2, wherein the compression spring is biased following at least part of the predetermined amount of rotation of the actuator.

5. The transseptal medical device of claim 2, wherein the compression spring is unbiased when the actuator has completed the predetermined amount of rotation.

6. The transseptal medical device of claim 1, wherein the torsion spring is biased when the actuator is in the first actuator orientation.

7. The transseptal medical device of claim 6, wherein the torsion spring is unbiased when the actuator has completed the predetermined amount of rotation.

8. The transseptal medical device of claim 1, wherein the needle control mechanism is disposed at the proximal end of the dilator.

9. The transseptal medical device of claim 1, wherein the medical device is disposed within an inner lumen of a sheath, the sheath having a proximal end and a distal end.

10. The transseptal medical device of claim 1, further comprising a valve or access port for introduction or removal of fluids.

11. The transseptal device of claim 1, wherein the needle control mechanism further comprises one or more components selected from the group consisting of a compression spring, a spacer, or a locking mechanism.

12. The transseptal device of claim 1, wherein the needle control mechanism further comprises a compression spring, wherein the compression spring is adapted to be compressed when the distal end of the needle is in a first position within the dilator and further wherein the compression spring is adapted to be decompressed when the distal end of the needle is in a second position external to the dilator.

13. The transseptal medical device of claim 1, wherein the actuator further comprises a member with an oblong shape, the oblong shape comprising the following:

a first edge adapted to engage the latch when the actuator is in the first actuator orientation; and a second edge adapted to avoid the latch when the actuator is in the second actuator orientation.

* * * * *